(12) United States Patent
Kamins et al.

(10) Patent No.: US 7,236,242 B2
(45) Date of Patent: Jun. 26, 2007

(54) NANO-ENHANCED RAMAN SPECTROSCOPY-ACTIVE NANOSTRUCTURES INCLUDING ELONGATED COMPONENTS AND METHODS OF MAKING THE SAME

(75) Inventors: Theodore I. Kamins, Palo Alto, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 345 days.

(21) Appl. No.: 11/044,105

(22) Filed: Jan. 27, 2005

(65) Prior Publication Data

US 2006/0164634 A1 Jul. 27, 2006

(51) Int. Cl.
G01N 21/65 (2006.01)
G01J 3/44 (2006.01)

(52) U.S. Cl. .................................................. 356/301
(58) Field of Classification Search ................. 356/301
See application file for complete search history.

(56) References Cited

U.S. PATENT DOCUMENTS

| | | | |
|---|---|---|---|
| 4,674,878 A | 6/1987 | Vo-Dinh | |
| 4,944,985 A | 7/1990 | Alexander et al. | |
| 5,017,007 A | 5/1991 | Milne et al. | |
| 5,255,067 A | 10/1993 | Carrabba et al. | |
| 5,527,712 A | 6/1996 | Sheehy | |
| 5,609,907 A | 3/1997 | Natan | |
| 5,772,905 A | 6/1998 | Chou | |
| 5,837,552 A | 11/1998 | Cotton et al. | |
| 6,027,968 A | 2/2000 | Nguyen et al. | |
| 6,149,868 A | 11/2000 | Natan et al. | |
| 6,165,911 A | 12/2000 | Calveley | |
| 6,294,450 B1 | 9/2001 | Chen et al. | |
| 6,365,059 B1 | 4/2002 | Pechenik | |
| 6,406,777 B1 | 6/2002 | Boss et al. | |
| 6,407,443 B2 | 6/2002 | Chen et al. | |
| 6,432,740 B1 | 8/2002 | Chen | |
| 6,623,977 B1 | 9/2003 | Farquharson et al. | |
| 6,649,683 B2 | 11/2003 | Bell | |
| 6,743,368 B2 | 6/2004 | Lee | |
| 6,773,616 B1 | 8/2004 | Chen et al. | |
| 2002/0142480 A1 | 10/2002 | Natan | |
| 2003/0120137 A1 | 6/2003 | Pawluczyk | |
| 2003/0203502 A1 | 10/2003 | Zenhausem et al. | |
| 2003/0231304 A1 | 12/2003 | Chan et al. | |
| 2004/0135997 A1 | 7/2004 | Chan et al. | |

OTHER PUBLICATIONS

Drew, Christopher, et al., "Metal Oxide-Coated Polymer Nanofibers," Nano Lett., vol. 3, No. 2, 2003, pp. 143-147.

Emory, Steven R., et al., "Screening and Enrichment of Metal Nanoparticles with Novel Optical Properties," J. Phys. Chem. B, vol. 102, No. 3, 1998, pp. 493-497.

(Continued)

Primary Examiner—F. L. Evans

(57) ABSTRACT

An NERS-active structure is disclosed that includes a substrate and at least one elongated component disposed on the substrate. The at least one elongated component may include two conducting strips including an NERS-active material and an insulating strip positioned between the two conducting strips. Alternatively, the at least one elongated component may include a homogeneous component. An NERS system is also disclosed that includes an NERS-active structure. Also disclosed are methods for forming an NERS-active structure and methods for performing NERS with NERS-active structures.

17 Claims, 10 Drawing Sheets

OTHER PUBLICATIONS

Felidj, N., et al., "Enhanced substrate-induced coupling in two-dimensional gold nanoparticle arrays," Physical Review B 66, 2002, pp. 245407-1 through 245407-7.

Felidj, N., et al., "Optimized surface-enhanced Raman scattering on gold nanoparticle arrays," Appl. Phys. Lett., vol. 82, No. 18, May 5, 2003, pp. 3095-3097.

Green, Mino, et al., "SERS Substrates Fabricated by Island Lithography: The Silver/Pyridine System," J. Phys. Chem. B, vol. 107, No. 47, 2003, pp. 13015-13021.

Kamins, T.I., et al., "Chemically vapor deposited Si nanowires nucleated by self-assembled Ti islands on patterned and unpatterned Si substrates," Physica E 13, 2002, pp. 995-998.

Kneipp, Katrin, et al., "Single Molecule Detection Using Surface-Enhanced Raman Scattering (SERS)," Physical Review Letters, vol. 78, No. 9, Mar. 3, 1997, pp. 1667-1670.

Liu, Feng-Ming, et al., "Efficient SERS substrates made by electroless silver deposition into patterned silicon structures," J. Mater. Chem., vol. 14, 2004, pp. 1526-1532.

Michaels, Amy M., et al., "Surface Enhanced Raman Spectroscopy of Individual Rhodamine 6G Molecules on Large Ag Nanocrystals," J. Am. Chem. Soc., vol. 121, No. 43, 1999, pp. 9932-9939.

Pinto, N.J., et al., "Electroless Deposition of Thin Metallic Films on Polymer Fibers Prepared via Electrospinning," Polymer Preprints, vol. 44, No. 2, 2003, pp. 138-139.

Tao, Andrea, et al., "Langmuir-Blodgett Silver Nanowire Monolayers for Molecular Sensing Using Surface-Enhanced Raman Spectroscopy," Nano Lett., vol. 3, No. 9, 2003, pp. 1229-1233.

NANO-ENHANCED RAMAN SPECTROSCOPY-ACTIVE NANOSTRUCTURES INCLUDING ELONGATED COMPONENTS AND METHODS OF MAKING THE SAME

FIELD OF THE INVENTION

The invention relates to nano-enhanced Raman spectroscopy (NERS). More particularly, the invention relates to NERS-active structures including features having nanoscale dimensions, methods for forming NERS-active structures, and methods for performing NERS using NERS-active structures.

BACKGROUND OF THE INVENTION

Raman spectroscopy is a well-known technique for performing chemical analysis. In conventional Raman spectroscopy, high intensity monochromatic light provided by a light source, such as a laser, is directed onto an analyte (or sample) that is to be chemically analyzed. A majority of the incident photons are elastically scattered by the analyte molecule. In other words, the scattered photons have the same energy, and thus the same frequency, as the photons that were incident on the analyte. However, a small fraction of the photons (i.e., about 1 in $10^7$ photons) are inelastically scattered by the analyte molecules. These inelastically scattered photons have a different frequency than the incident photons. This inelastic scattering of photons is termed the "Raman effect." The inelastically scattered photons may have frequencies greater than or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against their frequency. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to conventional Raman spectroscopy. In SERS, the analyte molecules are adsorbed onto, or placed adjacent to, a Raman-active metal surface or structure (a "SERS-active structure"). The interactions between the molecules and the structure cause an increase in the strength of the Raman signal. The mechanism of Raman signal enhancement exhibited in SERS is not completely understood. Two main theories of enhancement mechanisms have been presented in the literature: electromagnetic enhancement and chemical (or "first layer") enhancement. (For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932-39 (1999)).

Several SERS-active structures have been employed in SERS techniques, including active electrodes in electrolytic cells, active metal colloid solutions, and active metal substrates such as a roughened metal surface or metal "islands" formed on a substrate. For example, it has been shown that adsorbing analyte molecules onto or near a specially roughened metal surface made from gold or silver may enhance the effective Raman scattering intensity by factors of between $10^3$ and $10^6$ when averaged over the illuminated area of the sample.

Recently, Raman spectroscopy has been performed employing randomly oriented nanostructures, such as nanometer scale needles, particles, and wires, as opposed to a simple roughened metallic surface. This process will be referred to hereinafter as nano-enhanced Raman spectroscopy (NERS) The intensity of the Raman scattered photons from a molecule adsorbed on such a nanostructure may be increased by factors as high as $10^{14}$. Thus, the intensity of Raman scattered photons could be increased over what is obtained presently if there was a method for forming NERS-active structures that included nanoscale features having well controlled size, shape, location, and orientation. Also, the inability to produce such NERS-active structures is impeding research directed to completely understanding the enhancement mechanisms and, therefore, the ability to optimize the enhancement effect. In addition, NERS-active structures require significant time and money to fabricate. If these problems can be overcome, the performance of nanoscale electronics, optoelectronics, and molecular sensors may be significantly improved.

Accordingly, there is a need for NERS-active structures that include nanoscale features having well controlled size, shape, location, and orientation, and methods for their manufacture. In addition, there is a need for methods for producing high quantities of such NERS-active structures at relatively low cost.

BRIEF SUMMARY OF THE INVENTION

The present invention, in a number of embodiments, includes NERS-active structures, including features having nanoscale dimensions, methods for forming NERS-active structures, and methods for performing NERS using NERS-active structures.

An NERS-active structure is disclosed that includes a substrate and at least one elongated feature disposed on the substrate. The at least one elongated feature includes two conducting strips including an NERS-active material and an insulating strip positioned between the two conducting strips.

An NERS system is disclosed that includes an NERS-active structure, a light source configured to irradiate light onto the NERS-active structure, and a detector configured to receive Raman-scattered light scattered by an analyte when the analyte is located adjacent the NERS-active structure. The NERS-active structure includes a substrate and at least one feature disposed on the substrate. The at least one elongated feature includes two conducting strips including an NERS-active material and an insulating strip positioned between the two conducting strips.

A method for performing NERS is disclosed that includes the steps of providing an NERS-active structure, providing an analyte adjacent the NERS-active structure, irradiating the analyte and the NERS-active structure with excitation radiation, and detecting Raman scattered radiation scattered by the analyte. The NERS-active structure includes a substrate and at least one feature disposed on the substrate. The at least one elongated feature includes two conducting strips including an NERS-active material and an insulating strip positioned between the two conducting strips.

Also disclosed is a method for forming an NERS-active structure. The method includes: providing a substrate and forming a sacrificial structure on a surface of the substrate, the sacrificial structure having nanoscale or microscale dimensions; forming an insulating layer on the substrate and the sacrificial layer; directionally etching the insulating layer to form insulator sidewalls; removing the sacrificial structure; forming a conducting layer on the substrate and the insulator sidewalls; and directionally etching the conducting layer to form conducting sidewalls of NERS-active material.

Another method for forming an NERS-active structure is disclosed. The method includes: forming a superlattice structure comprising a plurality of layers of a first material and a plurality of layers of a second material, the first material having different etching characteristics than the second material; etching the plurality of layers of the first material laterally from one end relative to the layers of the second material to form a mold having recesses of the first material and protrusions of the second material at the one end, the recesses and the protrusions having nanoscale dimensions; providing a substrate, the substrate having a surface; applying a layer of deformable material to the surface of the substrate; pressing the mold against the substrate, the protrusions of the second material forming an array of corresponding recesses in the layer of deformable material; removing at least a portion of the layer of deformable material to expose at least a portion of the underlying substrate; applying a layer of NERS-active material to the substrate, the layer of NERS-active material covering a remaining portion of the layer of deformable material and the exposed portion of the underlying surface of the substrate; and removing the remaining portion of the layer of deformable material and the overlying portion of the NERS-active material to form extended protrusions of NERS-active material.

Yet another method for forming an NERS-active structure is disclosed. The method includes: forming a superlattice structure comprising a plurality of layers of a first material and a plurality of layers of a second material, the first material having different etching characteristics than the second material; etching the plurality of layers of the first material laterally from one end relative to the layers to form a mold having recesses of the first material and protrusions of the second material at the one end, the recesses and the protrusions having nanoscale dimensions; providing a substrate, the substrate having a surface; applying a layer of NERS-active material to the surface of the substrate; applying a layer of deformable material over the NERS-active material; pressing the mold against the substrate, the protrusions of the second material forming an array of corresponding recesses in the layer of deformable material; removing at least a portion of the layer of NERS-active material to expose at least a portion of the underlying surface of the substrate and form extended protrusions of NERS-active material; and removing the layer of deformable material.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes NERS-active structures including elongated features having nanoscale dimensions, methods for forming NERS-active structures, NERS systems including NERS-active structures, and methods for performing NERS using such systems.

The methods disclosed herein are drawn to the fabrication of NERS-active structures, including nanoscale features having well controlled size, shape, and spacing, which allows for improved enhancement of the Raman scattered signal intensity relative to previous NERS-active structures.

It should be understood that the illustrations presented herein are not meant to be actual views of any particular NERS-active structure, but are merely idealized representations which are employed to describe the present invention.

Additionally, for ease of discussion, elements common to FIGS. 1 through 7 retain the same numerical designation.

Figure 1:
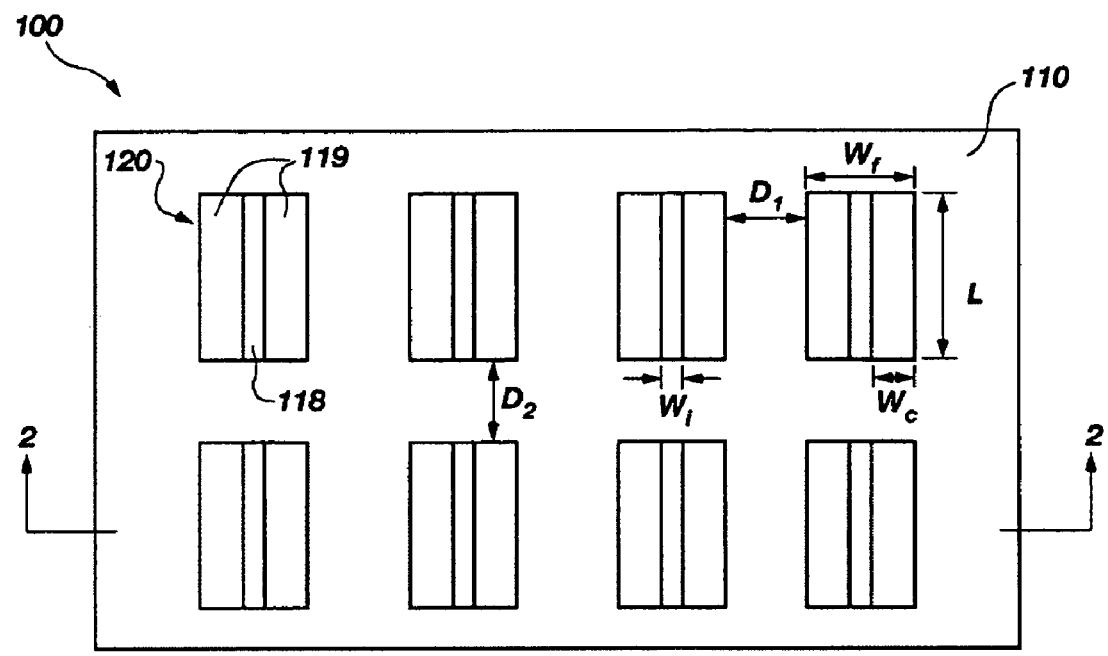
FIG. 1 is a top view of an exemplary embodiment of an NERS-active structure according to the invention.
Figure 2:
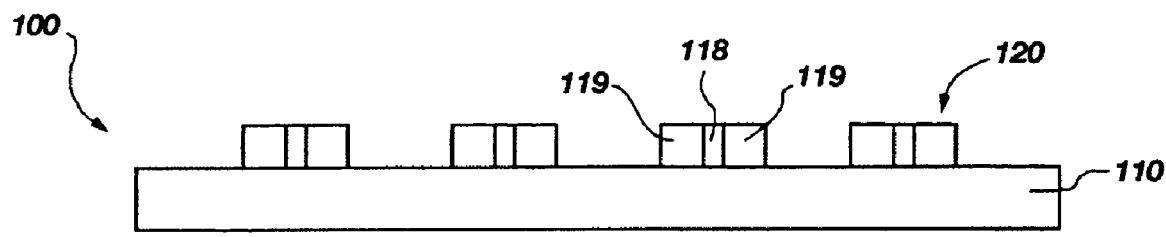
FIG. 2 is a cross-sectional view of the NERS-active structure of FIG. 1 taken along line 2-2.

An exemplary embodiment of an NERS-active structure according to the invention is shown in FIGS. 1 and 2. An NERS-active structure 100 includes a substrate 110 and an elongated component in the form of at least one elongated feature 120 disposed on the substrate 110. The at least one elongated feature 120 may have a length L one or two orders of magnitude greater than a width $W_f$. The at least one elongated feature 120 includes an insulating strip 118 formed from a first material and two conducting strips 119 including an NERS-active material.

The at least one elongated feature 120 has a width between about 2 and about 130 nanometers, preferably between about 4 and about 45 nanometers. The insulating strip 118 of the elongated feature 120 may have width $W_i$ of between about 0.5 and about 50 nanometers, preferably between about 0.5 and about 5 nanometers. In addition, the width of the insulating strip may be selected to correspond to the size of a particular analyte molecule to be analyzed with the NERS-active structure 100, such that the molecule is capable of being adsorbed on the insulating strip 118. Each conducting strip 119 of the elongated structure 120 may have a width $W_c$ of between about 1 and about 40 nanometers, preferably between about 2 and about 20 nanometers. Such an elongated feature 120 may enhance the Raman signal emitted by the analyte molecule.

The substrate 110 of the NERS-active structure 100 may be formed from, for example, silicon or germanium, or from III-V or II-VI semiconductor materials. The substrate may alternatively be formed from an insulating material, such as silicon dioxide or silicon nitride. Silicon dioxide on a silicon wafer is one example of an insulating substrate. Any suitable substrate material may be used, as long as the material does not fluoresce at the wavelength emitted by an excitation wavelength source employed in an NERS system. The insulating strip 118 of the at least one elongated feature 120 may be formed from any nonconductive material including, but not limited to, silicon dioxide, silicon nitride, silicon oxynitride, or aluminum oxide. The conducting strip 119 of the at least one elongated feature 120 may include any NERS-active material such as, for example, gold, silver, copper, platinum, palladium, aluminum, or any other material that will enhance the Raman scattering of photons by analyte molecules positioned adjacent thereto.

Referring to FIGS. 1 and 2, the NERS-active structure 100 may include a plurality of elongated features 120 disposed in an array on a surface of the substrate 110, each elongated feature 120 of the array being disposed at a predetermined location on the surface of the substrate 110. The exemplary NERS-active structure 100 includes elongated features 120 formed in rows and columns, each elongated feature 120 laterally separated from adjacent elongated features by a predetermined distance D (shown as $D_1$ and $D_2$ in FIG. 1). The predetermined distance $D_1$ may be between about 10 and about 100 nanometers. The elongated features 120 may be separated distally (end-to end) by a predetermined distance $D_2$, between about 10 and about 100 nanometers.

Figure 3A:
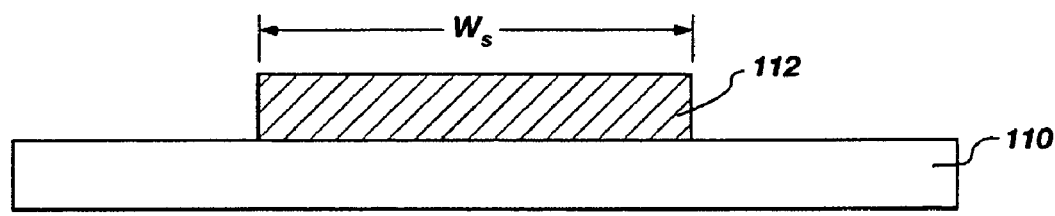
FIGS. 3A-3F illustrate an exemplary method for forming the NERS-active structures of FIGS. 1-2.

An exemplary method for making the NERS-active structure 100 is illustrated in FIGS. 3A–3F. To produce the NERS-active structure 100, a substrate 110 may be provided as shown in FIG. 3A. The substrate 110 may include a wafer or die of any suitable substrate material. Next, a sacrificial structure 112 is formed on a surface of the substrate 110 as shown in FIG. 3A. Various methods for forming a sacrificial structure 112 on a surface of a substrate are known in the art of microdevice fabrication. For example, a sacrificial layer may be deposited using physical vapor deposition or chemical vapor deposition, and the sacrificial layer may be defined using lithography or nanoimprinting. The width of the sacrificial structure $W_s$ may correspond to the predetermined distance $D_1$ of FIG. 1, the lateral separation between the elongated features 120, plus twice the width $W_c$ of the conducting strips 119, described hereinbelow.

Figure 3B:
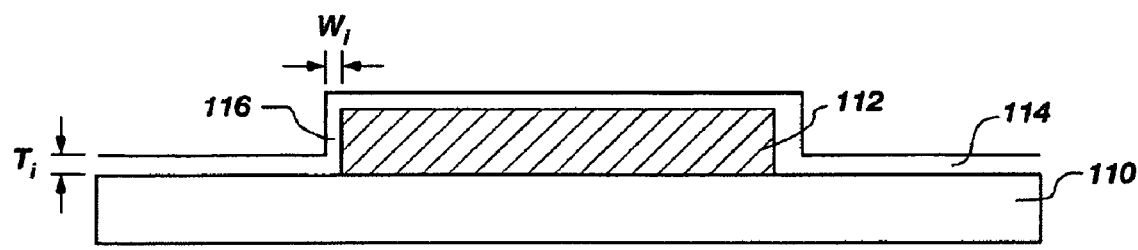
Figure 3C:
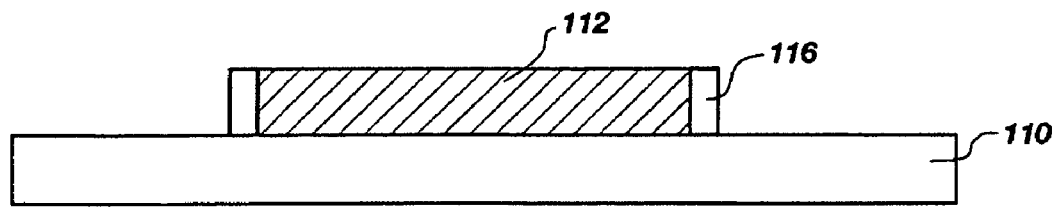

An insulating layer 114 is deposited over the substrate 110 and the sacrificial structure 112, as shown in FIG. 3B. The insulating layer 114 includes insulator sidewalls 116 on either side of the sacrificial structure 112. The insulating layer 114 may be etched using a directional etch such as a reactive ion etch (RIE) to form the structure shown in FIG. 3C. The width $W_i$ of the insulator sidewalls 116 corresponds to the thickness $T_i$ of the insulating layer 114. Although the width $W_i$ of the insulator sidewalls does not necessarily equal the thickness $T_i$ of the insulating layer 114, the ratio between the two is constant. Wider insulator sidewalls 116 may therefore be formed using a thicker insulating layer 114. The width $W_i$ of the insulator sidewalls 116 (FIG. 3B) corresponds to the width $W_i$ of the insulating strips 118 (FIG. 1), and is preferably between 0.5 and about 5 nanometers.

Figure 3D:
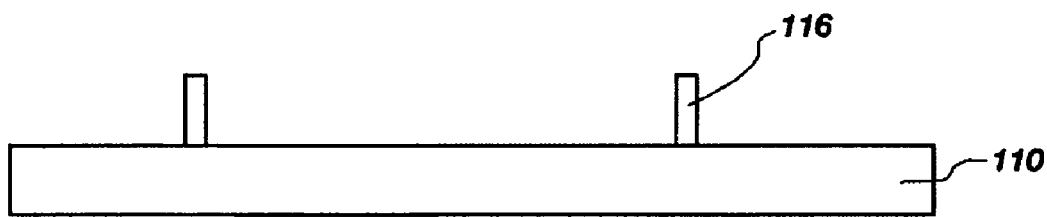
Figure 3E:
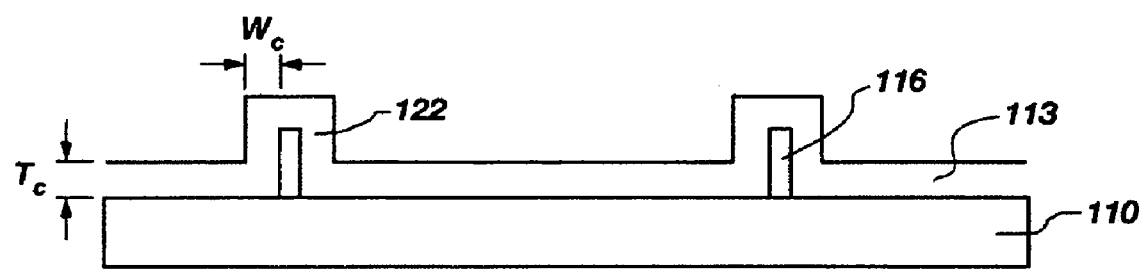
Figure 3F:
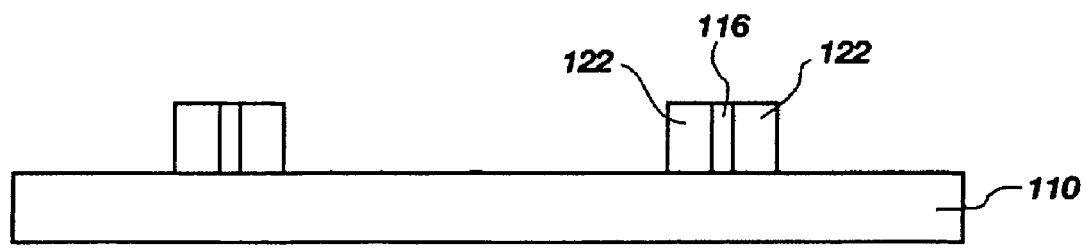

A selective etch is performed, removing sacrificial structure 112, as shown in FIG. 3D. Insulator sidewalls 116 remain. A conducting layer 113 is deposited over the insulator sidewalls 116, as shown in FIG. 3E. The conducting layer 113 includes conductor sidewalls 122 on either side of each insulator sidewall 116. The conducting layer 113 may be etched using a directional etch such as a reactive ion etch (RIE) to form the structure shown in FIG. 3F. The width $W_c$ of the conductor sidewalls 122 corresponds to the thickness $T_c$ of the conducting layer 113. Wider conductor sidewalls 122 may be formed using a thicker conducting layer 113. The width $W_c$ of the conductor sidewalls 122 (FIG. 3E) corresponds to the width $W_c$ of the conducting strips 119 (FIG. 1), and is preferably between about 2 and about 20 nanometers The conductor sidewalls 122, and the insulator sidewalls 116, may be defined lengthwise (in the orthogonal direction of FIG. 3F) by conventional photolithography or lithography techniques, or by nanoimprint lithography, also known as non-conventional lithography thereby forming the conducting strips 119 and the insulating strips 118, as shown in top view in FIG. 1. Optionally, the insulating strips 118 may be selectively etched, such that the analyte molecule to be analyzed with the NERS-active structure 100 is capable of draping between two adjacent conducting strips 119, part of the molecule being adsorbed on a first conducting strip 119 and another part of the molecule being adsorbed on a second, adjacent conducting strip 119. In another embodiment, the insulating strips 118 may be either indiscriminately or specifically purposefully activated to adsorb analyte molecules.

Figure 4:
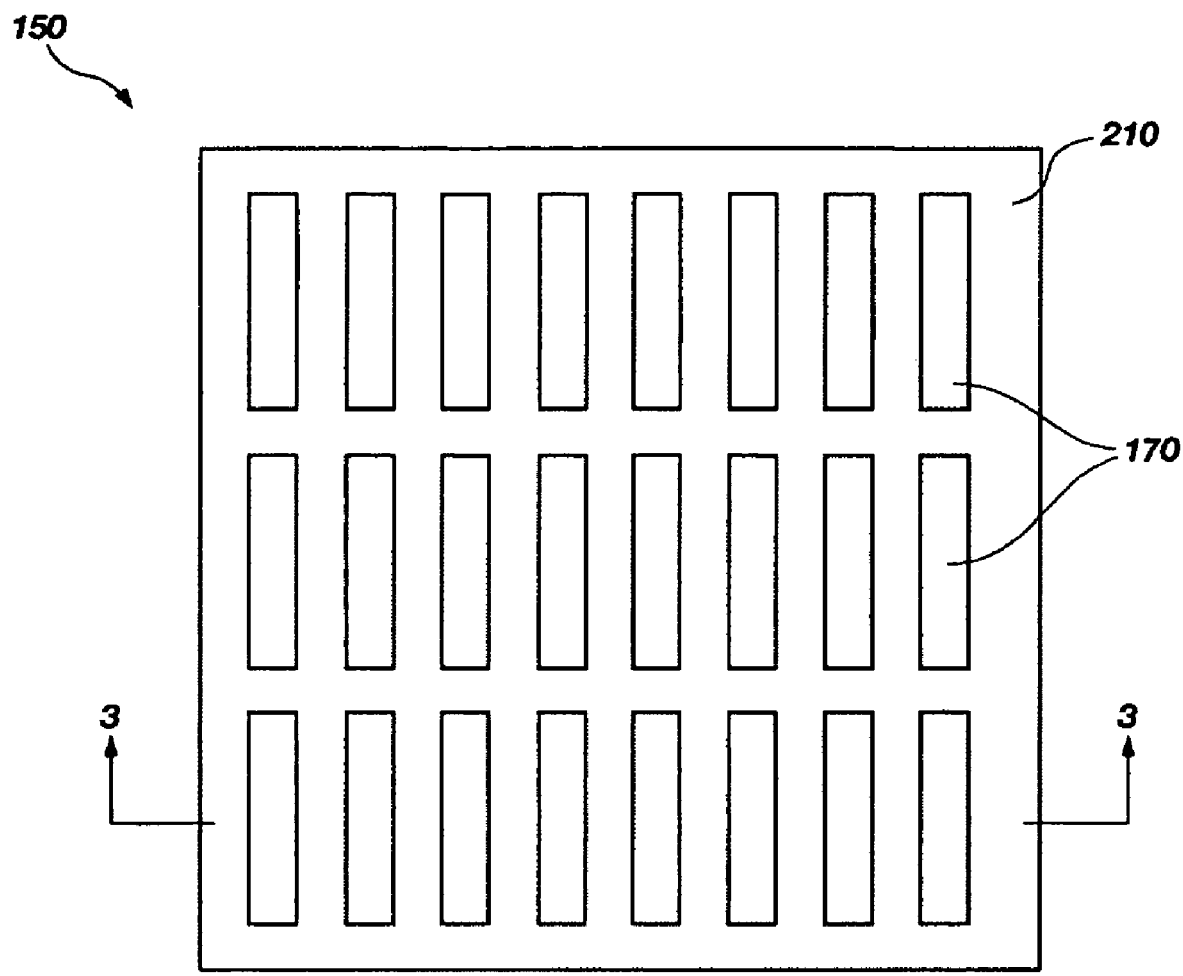
FIG. 4 is a top view of another exemplary embodiment of an NERS-active structure according to the invention.

Another exemplary embodiment of an NERS-active structure according to the invention is shown in FIG. 4. An NERS-active structure 150 includes a substrate 210 and a plurality of elongated components. The NERS-active structure 150 may be substantially similar to the NERS-active structure 100 shown in FIG. 1. However, each elongated component may include elongated elements 170 disposed on a surface of the substrate 210. At least some of the elongated elements 170 are laterally separated from adjacent elongated elements by a predetermined distance D between about 0.5 and about 20 nanometers, enabling an analyte molecule to be adsorbed between two elongated elements 170. The elongated elements 170 shown in FIG. 4 are arranged in a substantially evenly spaced array; however, the elongated elements 170 may be arranged in pairs, similar to the arrangement of the conducting strips 119 of the NERS-active structure 100, as shown in FIG. 1. The elongated elements 170 may be symmetrical or asymmetrical in shape, and formed of a substantially homogeneous material, as opposed to the strips of different material forming the elongated features 120 shown in FIGS. 1 and 2.

Figure 5A:
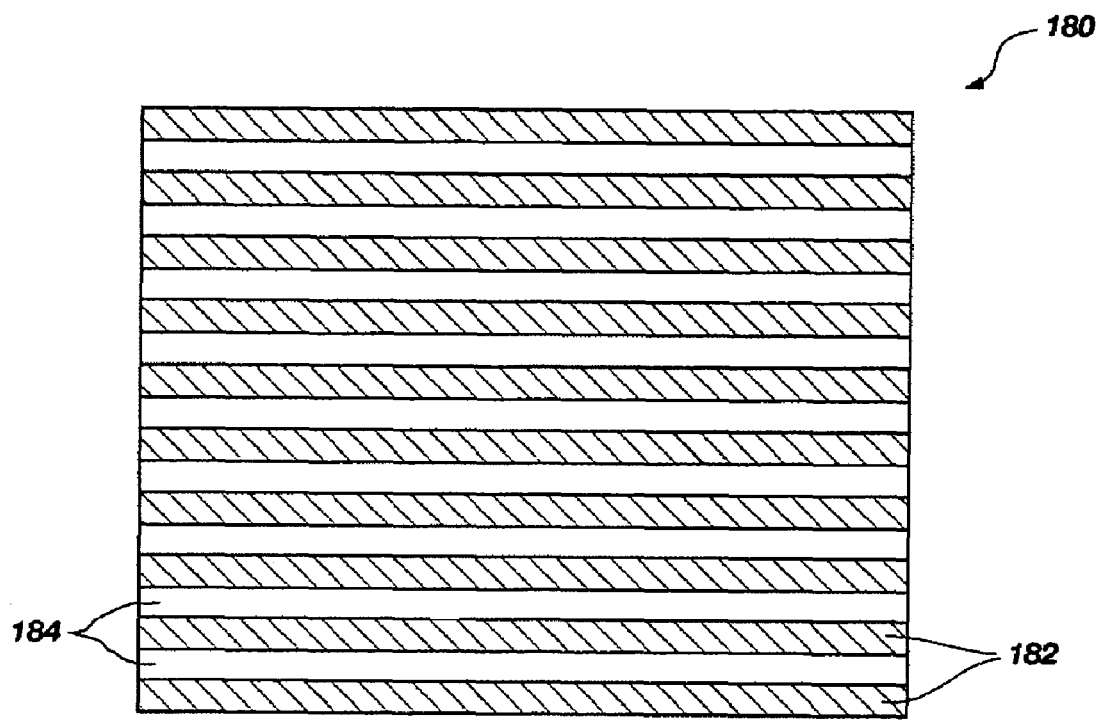
FIGS. 5A-5J illustrate an exemplary method for forming the NERS-active structures of FIG. 4.

An exemplary imprinting method for making the NERS-active structure 150 is illustrated in FIGS. 5A-5J. To produce the NERS-active structure 150, a superlattice structure 180 may be provided as shown in FIG. 5A. Superlattice structures are described in U.S. Pat. No. 6,407,443 to Chen, et al, which is assigned to the assignee of the present invention and is incorporated by reference in its entirety herein. The superlattice structure comprises alternating layers of a first material 182 and a second material 184. One conventional technique of forming the alternating layers of a superlattice structure is molecular beam epitaxy (MBE). This technique is characterized by the growth of thin films through the exceedingly slow evaporation of semiconductors or metals in a clean environment. The deposition rate achieved with MBE is generally only a few nanometers per minute. Another conventional technique for constructing superlattice structures is known as chemical vapor deposition (CVD), a process that involves the use of chemical reactions to create thin films of material on a substrate.

The alternating layers preferably comprise layers of materials having different etching characteristics. For example, the first material 182 may comprise silicon, and the second material 184 may comprise silicon-germanium—an alloy of silicon and germanium. Another exemplary combination of materials is silicon and silicon dioxide. Depending on the etchant used, either the silicon or the silicon dioxide could have a faster etch rate. Yet another exemplary combination of materials is a combination of III-V materials, such as gallium arsenide and $Al_{(x)}Ga_{(1-x)}As$, where X is in the range of 0.1-1 mole fraction aluminum, preferably in the range of 0.1-0.5 mole fraction aluminum.

Figure 5B:
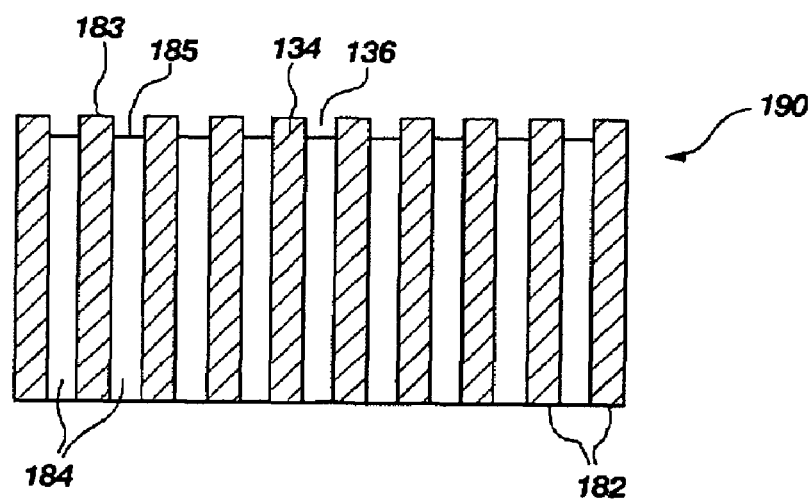

The superlattice structure 180 may be cross-sectioned and etched to form a nanoimprint mold 190, as shown in FIG. 5B. The exposed edges of the cross-sectioned superlattice structure 180 are etched with an etchant that attacks the second material 184 more rapidly than the first material 182. A surface 183 of the first material 182 thus protrudes above a recessed surface 185 of the second material 184. A plurality of protrusions 134 and recesses 136 consequently form the nanoimprint mold 190. The spacing and width of the protrusions 134 may be substantially similar to the width and spacing, respectively, of the elongated elements 170 (FIG. 4) to be formed.

Nanoimprinting techniques suitable for use in the present invention are described in U.S. Pat. No. 6,432,740 to Chen, which is assigned to the assignee of the present invention and is incorporated by reference in its entirety herein. Nanoimprinting utilizes compression molding and a pattern transfer process. Generally, the nanoimprint mold 190 having nanometer-scale protrusions 134 and recesses 136 is pressed into a thin deformable layer 138 (FIG. 5D) on a substrate 210 (FIG. 5C), which creates a thickness contrast pattern in the deformable layer, as shown in FIG. 5E. After the mold is removed (FIG. 5F), an etching process is used to transfer the pattern through the entire thickness of the deformable layer by removing the remaining thickness of the deformable layer in the compressed areas 146 so that regions of the underlying substrate are exposed (FIG. 5G).

Figure 5C:
Figure 5D:
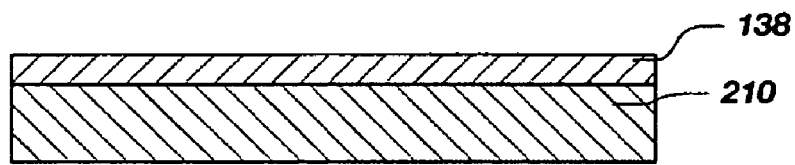
Figure 5E:
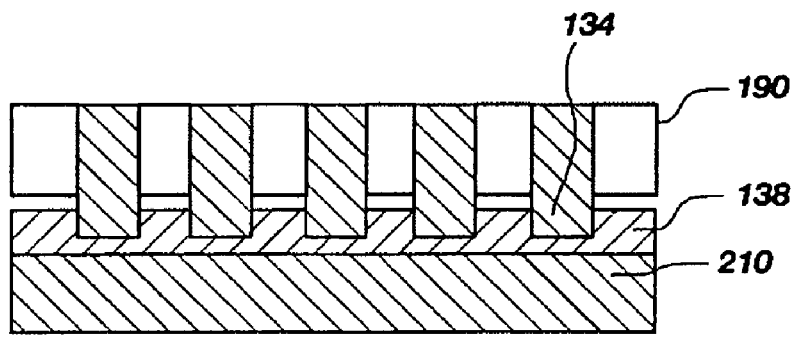
Figure 5F:
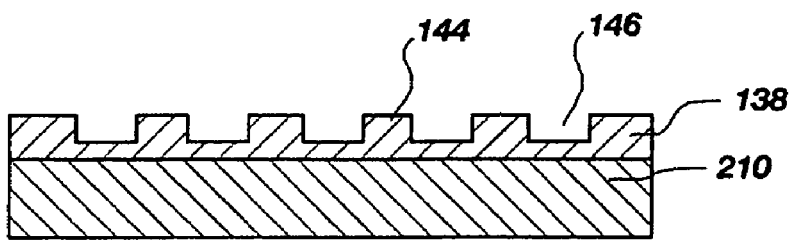
Figure 5G:
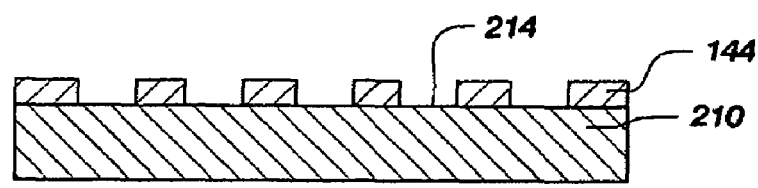
Figure 5H:
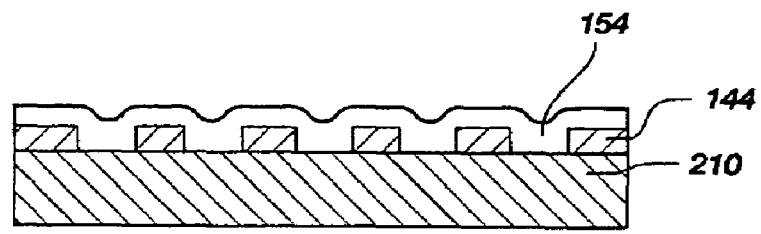

The material of the feature to be formed, such as the NERS-active material of the elongated component, is deposited on the partially covered substrate, as shown in FIG. 5H. The material is deposited by conventional techniques, such as by CVD, physical vapor deposition (PVD), sputtering, or electron beam evaporation. The NERS-active material may then be removed from selected regions by etching or by dissolving the deformable material to "lift off" the NERS-active material from these regions. Lift-off processes and etching processes are known in the art. Alternatively, the NERS-active material may be deposited before the deformable layer 138 is applied, as described hereinbelow, with reference to FIGS. 6A-6G

An NERS-active structure substrate 210 may be provided, and a layer 138 of deformable material may be applied to a surface thereof (FIG. 5C-5D). The layer 138 of deformable material may include a thermoplastic polymer such as, for example, poly(methyl methacrylate) (PMMA). The thickness of the layer 138 of deformable material may be approximately equal to, or slightly greater than, the height of the elongated components of the NERS-active structure to be formed (i.e., between about 1 and about 50 nanometers). The layer 138 of deformable material alternatively may include many other organic, inorganic, or hybrid materials that will deform under pressure of the mold 190 and that can be further processed, as described herein below.

As shown in FIG. 5E, the mold 190 may be pressed against the NERS-active structure substrate 210 such that the protrusions 134 of the mold 190 are pressed into the layer 138 of deformable material. The protrusions 134 and recesses 136 of the mold 190 may form corresponding recesses 146 and protrusions 144 in the layer 138 of deformable material, as shown in FIG. 5F. In one nanoimprinting technique, the layer 138 of deformable material may be softened by heating the layer 138 to a temperature above the glass transition temperature of the material prior to pressing the mold 190 against the NERS-active structure substrate 210. The mold 190 may be removed subsequent to cooling the layer 138 of deformable material to a temperature below the glass transition temperature of the material. Alternatively, the mold 190 may be removed prior to cooling the layer 138 of deformable material if the layer 138 will maintain its shape (i.e., maintain the recesses 146 and protrusions 144) until the temperature of the layer 138 drops below the glass transition temperature of the material. In an alternate technique, the deformable layer 138 is applied to the substrate 210 in the liquid-form. As the imprint mold 190 is pressed against the deformable layer 138, the material in the deformable layer 138 flows away from the regions compressed by the protrusions 134 of the mold 190. The remaining deformable layer 138 is then hardened by exposing the deformable layer 138 to ultraviolet light, which crosslinks the bonds in the deformable layer 138, and then the mold 190 is separated from the substrate 210.

At least a portion of the patterned layer 138 of deformable material may be removed by, for example, plasma etching, reactive ion etching or wet chemical etching, until regions 214 of exposed substrate material of the underlying NERS-active structure substrate 210 are exposed, as shown in FIG. 5G. A portion of the protrusions 144 of the layer 138 of deformable material may remain, and the underlying NERS-active structure substrate 210 may be exposed at the regions where the recesses 146 were previously located. Optionally, an additional NERS-active layer (not shown) may be deposited on the NERS-active structure substrate 210 prior to the formation of elongated elements 170. Therefore, the additional NERS-active layer may be exposed at the regions where the recesses 146 were previously located.

Figure 5I:
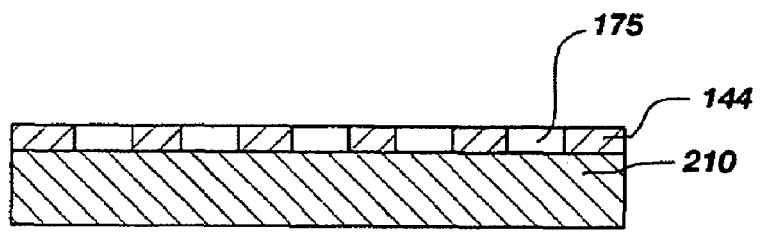

Referring to FIG. 5H, a layer 154 of NERS-active material such as, for example, gold, silver, copper, platinum, palladium, or aluminum, may be applied to the NERS-active structure substrate 210 over the remaining portion of the protrusions 144 of the layer 138 of deformable material and the regions 214 of exposed substrate. At least a portion of the layer 154 of NERS-active material may then be removed by, for example, chemical-mechanical polishing (CMP) until the protrusions 144 are exposed to provide a substantially smooth, flat surface, as shown in FIG. 5I. The remaining portion of the layer 154 of NERS-active material between the protrusions 144 of the layer 138 of deformable material comprises extended protrusions 175 on the surface of the substrate 210. The remaining portions of the protrusions 144 of the layer 138 of deformable material may be removed by, for example, plasma or reactive ion etching or wet chemical etching, until only extended protrusions 175 remain on the surface of the NERS-active structure substrate 210.

Alternatively, the NERS-active material can be removed from the regions containing the protrusions 144 of the deformable material by a "lift-off" process, in which the deformable layer is dissolved by a suitable solvent or etchant, detaching the overlaying NERS-active material from the substrate. The NERS-active material directly contacting the substrate is not significantly affected. The remaining deformable material may then be removed by, for example, plasma or reactive ion etching or wet chemical etching, until only extended protrusions 175 of the NERS-active material remain on the surface of the NERS-active structure substrate 210. The NERS-active material must be discontinuous for a "lift-off" process (not shown), with portions of sides of the protrusions 144 of the deformable material exposed to the solvent.

Figure 5J:
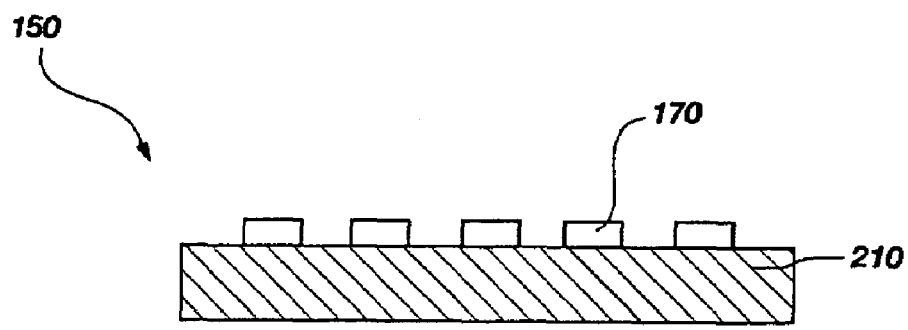

The length of the extended protrusions may be defined by conventional photolithography or lithography techniques or by nanoimprint lithography, thereby forming the elongated elements 170, as shown in top view in FIG. 4. A cross-section of the NERS-active structure 150 of FIG. 4, taken along line 3-3 is depicted in FIG. 5J. The NERS-active structure 150 then may be used in an NERS system to enhance the Raman signal of an analyte.

Figure 6A:
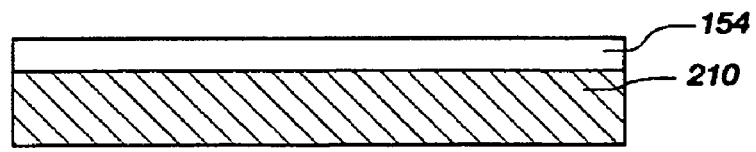
FIGS. 6A-6G illustrate another exemplary method for forming the NERS-active structures of FIG. 4
Figure 6B:
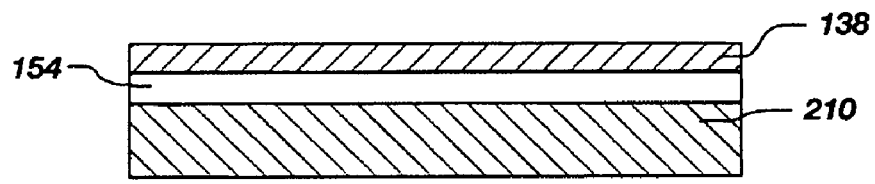
Figure 6C:
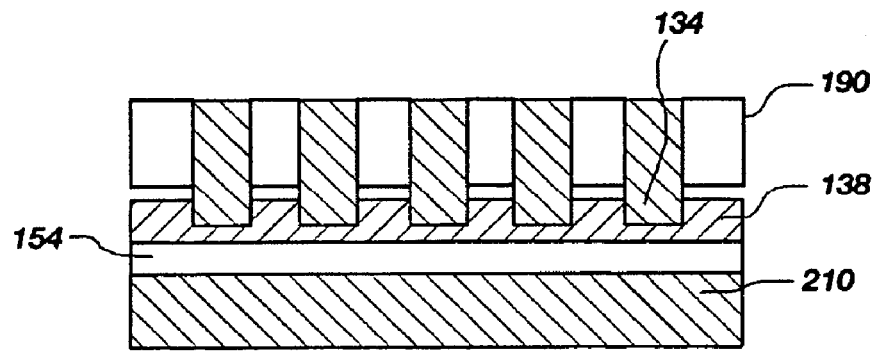
Figure 6D:
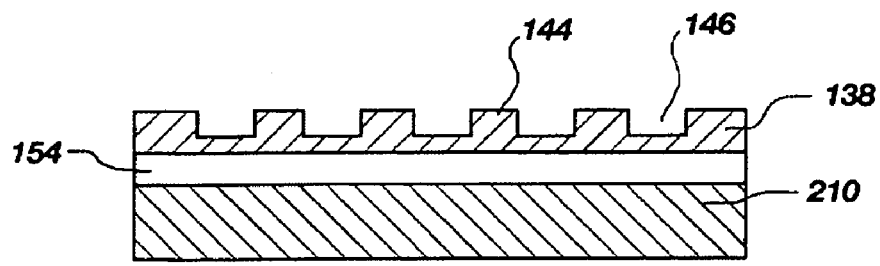
Figure 6E:
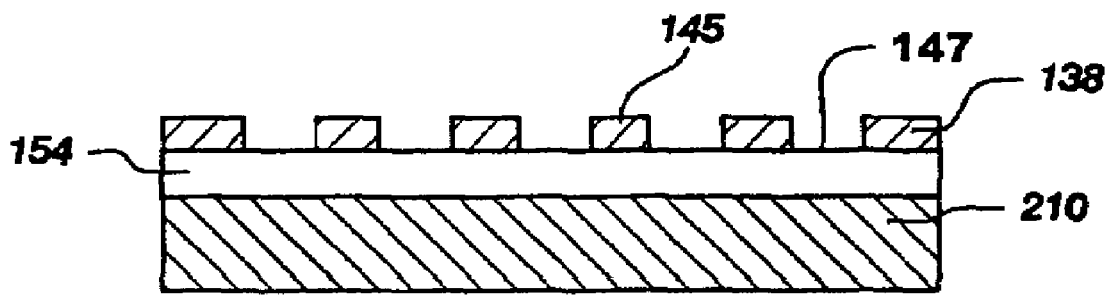

Another nanoimprinting technique suitable for use in the present invention is depicted in FIGS. 6A-6F. The NERS-active material 154 may be deposited directly on the substrate 210. The deformable layer 138 may be applied over the NERS-active material 154, as illustrated in FIG. 6B. The mold 190 may be pressed against the NERS-active structure substrate 210 such that the protrusions 134 of the mold are pressed into the layer 138 of deformable material (FIG. 6C). The protrusions 134 and recesses 136 of the mold 190 may form corresponding recesses 146 and protrusions 144 in the layer 138 of deformable material, as shown in FIG. 6D. At least a portion of the patterned layer 138 of deformable material may be removed until regions 147 of the NERS-active material 154 are exposed, as illustrated in FIG. 6E. A portion 145 of the layer 138 of deformable material may remain, where the protrusions 144 were previously located.

Figure 6F:
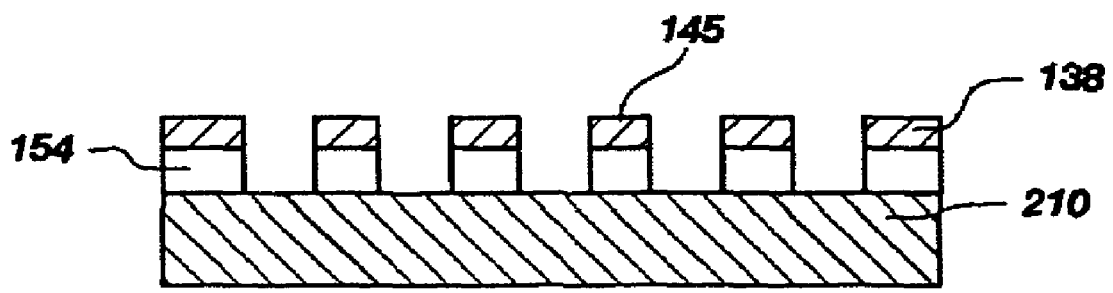
Figure 6G:
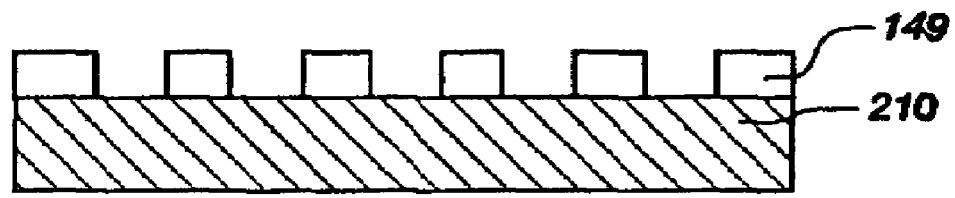

The exposed regions 147 of the NERS-active material 154 are then etched by a directional etch process, such as reactive ion etching, to remove the NERS-active material 154 from these regions as depicted in FIG. 6F. The remaining deformable material may then be removed until only extended protrusions 149 of the NERS-active material 154 remain on the surface of the NERS-active structure substrate 210. The length of the extended protrusions 149 may be defined, forming the elongated elements 170, as shown in top view in FIG. 4.

Figure 7:
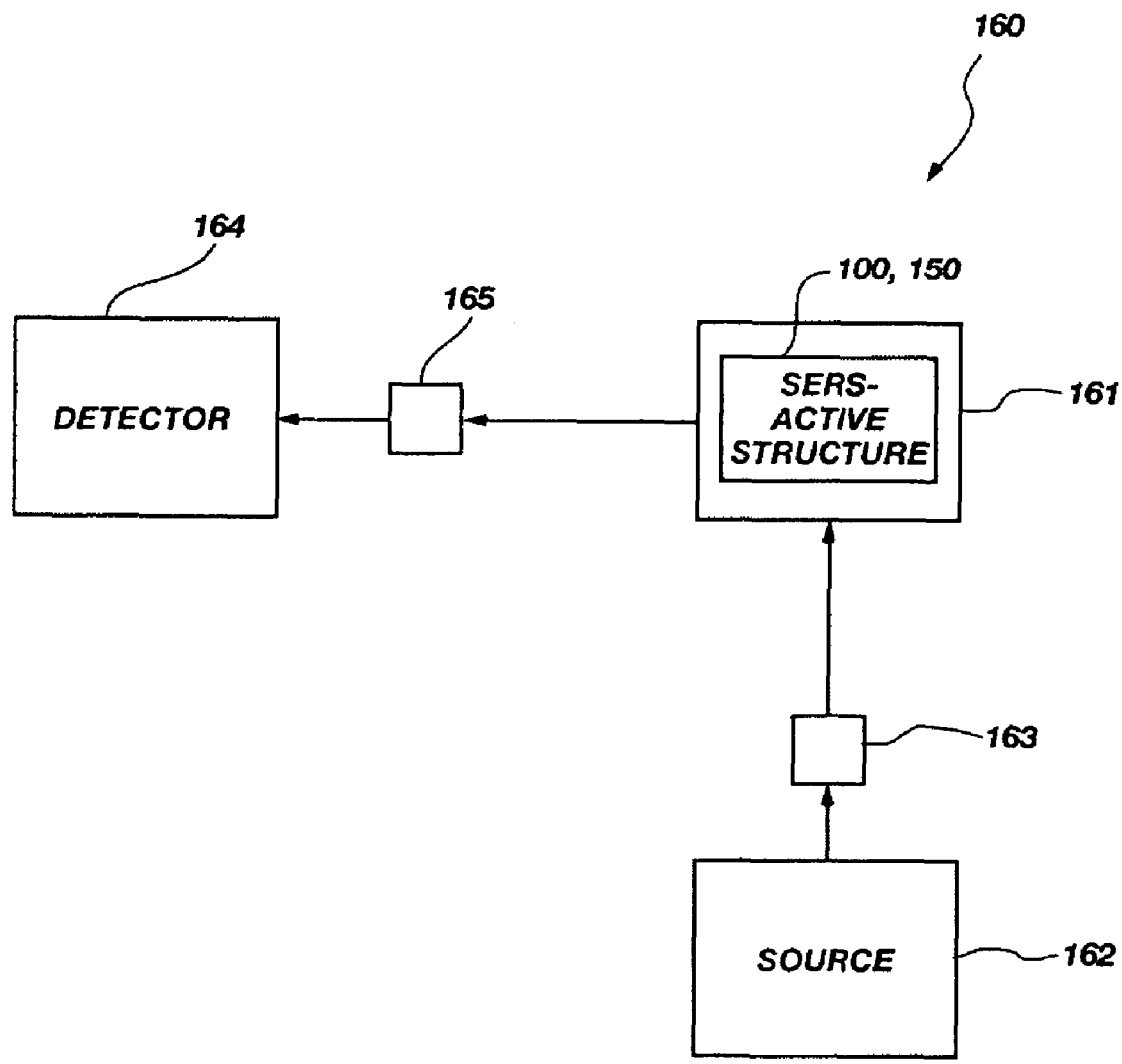
FIG. 7 is a schematic diagram of an exemplary system for performing surface enhanced Raman spectroscopy using the NERS-active structures of FIGS. 1-2 and 4.

An exemplary NERS system 160 according to the invention is illustrated schematically in FIG. 7. The system 160 may include one of the exemplary NERS-active structures 100 and 150, and may be used to perform enhanced Raman spectroscopy. The NERS system 160 may include a sample or analyte stage 161, an excitation radiation source 162, and a detector 164. The analyte stage 161 may include one of the NERS-active structure 100 and the NERS-active structure 150 (FIGS. 1-2 and 4). The NERS system 160 also may include various optical components 163 positioned between the excitation radiation source 162 and the analyte stage 161, and various optical components 165 positioned between the analyte stage 161 and the detector 164.

The excitation radiation source 162 may include any suitable source for emitting radiation at the desired wavelength, and may be capable of emitting a tunable wavelength of radiation. For example, commercially available semiconductor lasers, helium-neon lasers, carbon dioxide lasers, light emitting diodes, incandescent lamps, and many other known radiation-emitting sources may be used as the excitation radiation source 162. The wavelengths that are emitted by the excitation radiation source 162 may be any suitable wavelength for properly analyzing the analyte using NERS. An exemplary range of wavelengths that may be emitted by the excitation radiation source 162 includes wavelengths between about 350 nm and about 1000 nm.

The excitation radiation emitted by the source 162 may be delivered either directly from the source 162 to the analyte stage 161 and the NERS-active structure 100, 150. Alternatively, collimation, filtration, and subsequent focusing of the excitation radiation may be performed by optical components 163 before the excitation radiation impinges on the analyte stage 161 and the NERS-active structure 100, 150.

The NERS-active structure 100, 150 of the analyte stage 161 may enhance the Raman signal of the analyte, as discussed previously herein. In other words, irradiation of the NERS-active structure 100, 150 by excitation radiation may increase the number of photons inelastically scattered by an analyte molecule positioned near or adjacent to the NERS-active structure 100, 150.

The Raman scattered photons may be collimated, filtered, or focused with optical components 165. For example, a filter or a plurality of filters may be employed, either as part of the structure of the detector 164, or as a separate unit that is configured to filter the wavelength of the excitation radiation, thus allowing only the Raman scattered photons to be received by the detector 164.

The detector 164 receives and detects the Raman scattered photons and may include a monochromator (or any other suitable device for determining the wavelength of the Raman scattered photons) and a device such as, for example, a photomultiplier for determining the quantity of Raman scattered photons (intensity).

Ideally, the Raman scattered photons are scattered isotropically, being scattered in all directions relative to the analyte stage 161. Thus, the position of the detector 164 relative to the analyte stage 161 is not particularly important. However, the detector 164 may be positioned at, for example, an angle of 90° relative to the direction of the incident excitation radiation to minimize the intensity of the incident excitation radiation that may be incident on the detector 164.

To perform NERS using the system 160, a user may provide an analyte molecule or molecules adjacent to the elongated components of the NERS-active structure 100, 150. The analyte and the NERS-active structure 100,150 are irradiated with excitation radiation or light from the source 162. Raman scattered photons scattered by the analyte are then detected by the detector 164.

The structures and systems disclosed herein may also be used to perform enhanced hyper-Raman spectroscopy. When excitation radiation impinges on an analyte molecule, a very small number of photons may be scattered at frequencies corresponding to the higher order harmonics of the excitation radiation, such as the second and third harmonics (i.e., twice or three times the frequency of the excitation radiation). Some of these photons may have a frequency that is Raman-shifted relative to the frequencies corresponding to the higher order harmonics of the excitation radiation. These higher order Raman-scattered photons can provide information about the analyte molecule that cannot be obtained by first order Raman spectroscopy. Hyper-Raman spectroscopy involves the collection and analysis of these higher order Raman-scattered photons.

The methods disclosed herein allow for the reproducible formation of NERS-active structures including nanoscale features having well controlled size, shape, location, and orientation. These structures allow for improved enhanced Raman spectroscopy and may be used to produce molecular sensors having superior sensitivity and uniformity relative to conventional Raman spectroscopy. The performance of nanoscale electronics, optoelectronics, molecular sensors, and other devices employing the Raman effect may be significantly improved by using the NERS-active structures disclosed herein. In addition, the methods disclosed herein allow for production of high quantities and high densities per substrate surface area of NERS-active structures at relatively low cost.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. An NERS-active structure comprising:
   a substrate; and
   at least one elongated feature disposed on the substrate, the at least one elongated feature comprising:
   two conducting strips including an NERS-active material; and
   an insulating strip positioned between the two conducting strips.

2. The NERS-active structure of claim 1, wherein the insulating strip includes a nonconductive material.

3. The NERS-active structure of claim 2, wherein the insulating strip includes one of silicon dioxide, silicon nitride, silicon oxynitride, and aluminum oxide.

4. The NERS-active structure of claim 1, wherein the two conducting strips include one of gold, silver, copper, platinum, palladium, and aluminum.

5. The NERS-active structure of claim 1, wherein the elongated feature has a length of one or two orders of magnitude greater than a width of the elongated feature.

6. The NERS-active structure of claim 1, wherein the conducting strip has a width between about 2 nanometers and about 20 nanometers.

7. The NERS-active structure of claim 1, wherein the insulating strip has a width between about 0.5 nanometers and about 5 nanometers.

8. The NERS-active structure of claim 1, wherein the insulating strip has a width selected to correspond to the size of a particular analyte molecule to be analyzed with the NERS-active structure.

9. The NERS-active structure of claim 1, wherein the at least one elongated feature comprises a plurality of elongated features.

10. The NERS-active structure of claim 9, wherein each elongated feature is laterally separated from adjacent elongated features by a predetermined distance on a surface of the substrate.

11. The NERS-active structure of claim 10, wherein the plurality of elongated features comprises an array of elongated features.

12. The NERS-active structure of claim 1, wherein the substrate includes silicon.

13. The NERS-active structure of claim 1, further comprising an analyte molecule disposed on the insulating strip.

14. The NERS-active structure of claim 1, wherein the dimensions of the at least one elongated feature have a dimensional tolerance of less than about one nanometer.

15. An NERS system comprising:
   an NERS-active structure comprising:
   a substrate; and
   at least one elongated feature disposed on the substrate, the at least one elongated feature comprising:
   two conducting strips including an NERS-active material; and
   an insulating strip positioned between the two conducting strips;
   a light source configured to irradiate light onto the NERS-active structure; and
   a detector configured to receive Raman-scattered light scattered by an analyte located adjacent the NERS-active structure.

16. A method for performing NERS comprising:
   providing an NERS-active structure comprising:
   a substrate; and
   at least one elongated feature disposed on the substrate, the at least one elongated feature comprising:
   two conducting strips including an NERS-active material; and
   an insulating strip positioned between the two conducting strips;
   placing an analyte adjacent to the NERS-active structure;
   irradiating the analyte and the NERS-active structure with excitation radiation; and
   detecting Raman scattered radiation scattered by the analyte.

17. The method of claim 16, wherein the step of detecting comprises detecting Raman scatted radiation scattered by a single molecule.

* * * * *